(12) United States Patent
Watterson et al.

(10) Patent No.: US 6,521,736 B2
(45) Date of Patent: Feb. 18, 2003

(54) AMPHIPHILIC POLYMERIC MATERIALS

(75) Inventors: Arthur C. Watterson, Nashua, NH (US); Kunya Danprasert, Bangkapi (TH); Anil Diwan, West Haven, CT (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/952,883

(22) Filed: Sep. 14, 2001

(65) Prior Publication Data

US 2002/0099164 A1 Jul. 25, 2002

Related U.S. Application Data

(60) Provisional application No. 60/232,937, filed on Sep. 15, 2000.

(51) Int. Cl.$^7$ .............................................. C08G 63/02
(52) U.S. Cl. ........................ 528/272; 424/423; 424/448; 424/449; 424/499; 424/501
(58) Field of Search ................................ 528/271, 272; 424/501, 423, 499, 449, 448

(56) References Cited

PUBLICATIONS

Bundgaard (1986) "Design of Bioreversible Drug Derivatives and the Utility of the Double Prodrug Concept", Bioreversible Carriers in Drug Design Theory and Application Ch. 2, pp. 13–94.
Friis (1999) "Controlled–Release Oral Delivery Systems") in Polymer Preprints, American Cancer Society 40(1):252–369.
Erdmann et al. (1998) "Polymeric Prodrugs: Novel Polymers with Bioactive Components" in Tailored Polymeric Materials for Controlled Delivery Systems Ch 5 pp. 83–91.
Nagasaki et al. (1998) "The Reactive Polymeric Micelle, Convenient Tool for Targeting Drug Delivery System" in Tailored Polymeric Materials for Controlled Delivery Systems, American Chemical Society Ch 7 pp. 105–116.
Schwarte et al. (1998) "Cationic Hydrogels for Controlled Release of Proteins and Other Macromolecules" in Tailored Polymeric Materials for Controlled Delivery Systems, American Chemical Society Ch 3 pp. 56–66.
Shalaby (1998) "Injectable Absorbable Gel–Formers for the Controlled Release of Bioactive Agents–Drugs" in Tailored Polymeric Materials for Controlled Delivery Systems, American Chemical Society Ch 9 pp. 125–128.
Slomkowski et al. (1998) "Direct Synthesis of Polyester Microspheres, Potential Carriers of Bioactive Compounds" in Tailored Polymeric Materials for Controlled Delivery Systems, Ch 11 pp. 143–153.
Abuchowski et al. "Alteration of Immunological Properties of Bovine Serum Albumin by Covalent Attachment of Polyethylene Glycol", (1977) J. of Biol. Chem. 252(11):3578–3581.

Aldrovandi et al. "The SCID–hu Mouse As Model for HIV–1 Infection", (1993) Nature 363:732–736.
Alexander et al. "Investigation of (Oxodioxolenyl)methyl Carbamates as Nonchiral Bioreversible Prodrug Moieties for Chiral Amines", (1996) J. Med. Chem. 39:480–486.
Alexander et al. "(Acyloxy) alkyl Carbamates as Novel Bioreversible Prodrugs for Amines: Increased Permeation through Biological Membranes", (1988) J. Med. Chem. 31:318–322.
Alpegiani et al. "On The Preparation of 4–Hydroxymethyl–5–Methyl–1,3–Dioxol–2–One", (1992) Synth. Commun. 22(9):1277–1282.
Amado et al. "Reconstitution of Human Thymic Implants Is Limited by Human Immunodeficiency Virus Breakthrough during Antiretroviral Therapy", (1999) J. Virol. 73(8):6361–6369.
Berger et al. "Primary and Secondary Metabolism of Pentamidine by Rats", (1992) Antimicrob. Agents Chemother. 36(9):1825–1831.
Bonyhadi et al. "HIV Induces Thymus Depletion In Vivo", (1993) Nature 363:728–732.
Boykin et al. "2–5–Bis[4–(N–alkylamidino)phenyl]furans as Anti–*Pneumocystis carinii* Agents", (1998) J. Med. Chem. 41: 124–129.
Boykin et al. "Dicationic Diarylfurans as Anti–*Pneumocystis carinii* Agents", (1995) J. Med. Chem. 38:912–916.
Boykin et al. "Anti–Pneumocystis Activity of Bis–Amidoximes and Bis–O–Alkylamidoximes Prodrugs", (1996) Bioorg. Med. Chem. Lett. 6(24):3017–3020.
Bundgaard "Design and Application of Prodrugs" in Drug Design and Development, (1991) Harwood Academic Publ.: Switzerland pp. 113–191.
Bundgaard et al. "Esters of N,N–Disubstituted 2–Hydroxyacetamides as a Novel Highly Biolabile Prodrug Type for Carboxylic Acid Agents", (1987) J. Med. Chem. 30(3):451–454.
Bundgaard "Design of Prodrugs: Bioreversible Derivatives For Various Functional Groups and Chemical Entities" in Design of Produgs, (1985) Elsevier: Amsterdam, the Netherlands pp. 1–92.
Cardenas et al. "Antifungal Activities of Antineoplastic Agents: *Saccharomyces cerevisiae* as a Model System to Study Drug Action", (1999) Clin. Microbiol. Rev. 12(4):583–611.

(List continued on next page.)

*Primary Examiner*—Terressa M. Boykin
(74) *Attorney, Agent, or Firm*—Fish & Richardson PC

(57) ABSTRACT

The invention is based in part on the discovery of polymers that can complex with certain types of therapeutic drugs and transport those drugs across cell membranes in cell cultures with demonstrable therapeutic activity. The polymers are designed to overcome some of the known problems of liposomes as drug carriers. The polymers can be used in the development of physiologically stable, non-leaking, non-immunogenic, efficacious and safe targetable drug delivery systems (e.g., for delivery of anti-HIV or anticancer drugs).

44 Claims, No Drawings

OTHER PUBLICATIONS

Das et al. "Synthesis and Antiprotozoal Activity of 2,5–Bis(4–guanylpheny)furans", (1977) J. Med. Chem. 20(4):531–536.

Del Poeta et al. "In Vitro Antifungal Activities of a Series of Dication–Substituted Carbazoles, Furans, and Benzimidazoles", (1998) Antimicrob. Agents Chemother. 42(10):2503–2510.

Desormeaux et al. "Liposomes as Drug Delivery System: A Strategic Approach for the Treatment of HIV Infection", (1998) J. Drug Targeting 6(1):1–15.

Desormeaux et al. "Antiviral efficacy, intracellular uptake and pharmacokinetics of free and liposome–encapsulated 2',3'–dideoxyinosine", (1994) AIDS 8:1545–1553.

Douek et al. "Changes in thymic function with age and during the treatment of HIV infection", (1998) Nature 396:690–695.

Delgado et al. "The Uses and Propeties of PEG–Linked Proteins", (1992) Critical Reviews in Therapeutic Drug Carrier Systems 9(3,4):249–304.

Danprasert "Synthesis and Characterization of New Amphiphilic Polyesters Based on Poly(Ethylene Glycol)", (1999) Univ. of Massachusetts Lowell pp. 1–107.

Dreborg et al. "Immunotherapy With Monomethoxypolyethylene Glycol Modified Allergens", (1990) Crit. Rev. Ther. Drug Carrier Syst. 6(4):315–365.

El–Samaligy et al. "Ocular Disposition of Nanoencapsulated Acyclovir and Ganciclovir via Intravitreal Injection in Rabbit's Eye", (1996) Drug Delivery 3:93–97.

Ennis et al. "Structural Factors Influencing the Biodegradation of Imides", (1978) Appl. Environ. Microbiol. 35(1):51–53.

Fishman "Treatment of Infection Due to *Pneumocystis carnii*", (1998) Antimicrob. Agents and Chemother. 42(6):1309–1314.

Francesconi et al. "2,4–Diphenyl Furan Diamidines as Novel Anti–*Pneumocystis carinii* Pneumonia Agents", (1999) J. Med. Chem. 42:2260–2265.

Friis et al. "Design And Application of Produgs", (1996) $2^{nd}$ Eds. Overseas Publ.: Amsterdam, The Netherlands pp. 351–385.

Gelus et al. "Inhibition of HIV–1 Tat–TAR Interaction By Diphenylfuran Derivatives: Effects of the Terminal Basic Side Chains", (1999) Bioorganic & Medicinal Chemistry 7:1089–1096.

Hall et al. "Anti–Pneumocystis Activities of Aromatic Diamidoxime Prodrugs", (1998) Antimicrob. Agents Chemother. 42(3):666–674.

Halliday et al. "Inhibition of human immunodeficiency virus replication by the sulfonated stilbene dye resobene", (1996) Antiviral Research 33:41–53.

Jamieson et al. "In Vivo Pathogenesis of a Human Immunodeficiency Virus Type 1 Reporter Virus", (1998) J. Virol. 72(8):6520–6526.

Jones "Strategies of Antiviral Drug Discovery", (1998) Antivir. Chem. Chemother. 9:283–302.

Jones et al. "Novel Pentamidine Analogs in the Treatment of Experimental *Pneumocystis carinii* Pneumonia", (1990) Antimicrobial Agents and Chemotherapy 34(6):1026–1030.

Katre "The conjugation of proteins with polyethylene glycol and other polymers", (1993) Advanced Drug Delivery Review 10:91–114.

Kitchen et al. "HIV Type 1 Infection in Lymphoid Tissue: Natural History and Model Systems", (1998) AIDS Res. Hum. Retroviruses. Suppl. 3:S–235–239.

La et al. "Ply(ethylene glycol)–Based Micelles for Drug Delivery", (1997) in American Chemical Society Sym. Series 680 Ch. 7 99–116.

Llanos et al. "Does polyethylene oxide possess a low thrombogenicity?", (1993) J. Biomater. Sci. Polymer Ed. 4(4):381–400.

McConnaughie et al. "Design and Synthesis of RNA–Specific Groove–Binding Cations: Implications for Antiviral Drug Design", (1994) J. Med. Chem. 37:1063–1069.

McCune et al. "The SCID–hu Mouse: Murine Model for the Analysis of Human Hematolymphoid Differentiation and Function", (1988) Science 241:1632–1639.

McCune et al. "Suppresion of HIV Infection in AZT––Treated SCID–hu Mice", (1990) Science 247:564–566.

Merrill "Poly(Ethylene Oxide) and Blood Contact", (1992) Poly(Ethylene glycol) Chemistry: Biotechnical and Biomedical Application. Plenum Press NY pp. 199–220.

Miyauch et al. "Studies on Penem and Carbapenem. II. An Improved Synthesis . . . carboxylate", (1990) Chem. Pharm. Bull. 38(4):1077–1078.

Müller et al. "Profound and Sustained Inhibition of Platelet Aggregation by Fradafiban . . . in Men", (1997) Circulation 96:1130–1138.

Namikawa et al. "Infection of the SCID–hu Mouse by HIV–1", (1988) Science 242:1684–1687.

Namikawa et al. "Long–Term Human Hematopoiesis in the SCID–hu Mouse", (1990) J. Exp. Med. 172:1055–1063.

Okumura et al. "Poly(ethylene oxide)–Bearing Lipids and Interaction of Functionalized Liposomes with Intact Cells" in American Chemical Society Sym. Series (1997) 680 Ch. 6 pp. 82–98.

Park et al. "Hydrogels in Bioapplications" in American Cancer Society Sym. Series (1996) 680 Ch 1:1–10.

Paul et al. "Physicochemical Characteristics of Pentamidine–Loaded Polymethacrylate Nanoparticles: Implication . . . Mice", (1998) J. Drug Target 5:481–490.

Pettoello–Mantovani et al. "Saquinavir–Mediated Inhibition of Human Immunodeficiency Virus (HIV) . . . Tissues", (1997) Antimicrob. Agents Chemother. 41(9):1880–1887.

Pitman "Pro–Drugs of Amides, Imides, and Amines", (1981) Med. Res. Rev. 1(2):189–214.

Rabin et al. "Use of Standardized SCID–hu Thy/Liv Mouse Model for Preclinical Efficacy Testing of Anti–Human Immunodeficiency Virus Type 1 Compounds", (1996) Antimicrob. Agents Chemother. 40(3):755–762.

Rahmathullah et al. "Prodrugs for Amidines: Synthesis and Anti–*Pneumocystis carinii* Activity of Carbamates of 2,5–Bis(4–amidinophenyl)furan", (1999) J. Med. Chem. 42:3994–4000.

Sakamoto et al. "Studies on Prodrugs. VI. Preparation and Characterization of . . . Mecillinam", (1987) Chem. Pharm. Bull. 35:642–646.

Sakamoto et al. "Studies on Prodrugs. IV. Preparation . . . Norloxacin", (1985) Chem. Pharm. Bull. 33:4870–4877.

Sehon "Suppression of antibody responses by conjugates of antigens and monomethoxypoly(ethylene glycol)", (1991) Advanced Drug Delivery Reviews 6:203–217.

Sepkowitz et al. "Treatment of Opportunistic Infections in AIDS", (1995) Lancet 346:588–589.

Senior "Fate and Behavior of Liposomes In Vivo: A Review of Controlling Factors", (1987) CRC Critical Reviews in Therapeutic Drug Carrier Systems 3(2):123–193.

Shahrokh et al. "Stability of Alkoxycarbonylamidine Prodrugs", (1998) Pharm. Res. 15(3):434–441.

Silverman "Prodrugs and Drug Delivery Systems" in Ed. Academic Press, Inc. San Diego, Cal (1992) pp. 352–401.

Smith "The Process of New Drug Discovery and Development" in CRC Press, inc. Boca Raton, FL (1992) pp. 39–62.

Steck et al. "Trypanosoma rhodesiense: Evaluation of the Antitrypanosomal . . . Dihydrochloride", (1982) Exp. Parasitol. 53:133–144.

Verbiscar et al. "Carbamate Ester Latentiation of Physiologically Active Amines", (1970) J. Med. Chem. 13(6):1176–1179.

Warren et al. "Advances in the Treatment and Prohylaxis of *Pneumocystis carinii* Pneumonia", (1997) Pharmacotherapy 17(5):900–916.

Weller et al. "Orally Active Fibrinogen Receptor Antagonists 2. Amidoximes as Produgs of Amidines", (1996) J. Med. Chem. 39:3139–3146.

Wilson et al. "Evaluation of Drug–Nucleic Acid Interaction by Thermal Melting Curves", (1997) Methods Mol. Biol 90:219–240.

Wilson et al. "Design and Analysis of RNA Structure–Specific Agents as Potential Antivirals", (1996) J. Mol. Recognit. 9:187–196.

Withers–Ward et al. "Transient renewal of thymopoiesis in HIV–infected human thymic implants following antiviral therapy", (1997) Nat. Med. 3:1102–1109.

Wood et al. "1.5–Bis(4–amidinophenoxy) pentane (pentamidine) . . . sites", (1998) Eur. J. Pharmacol. 353:97–103.

Wood et al. "Pentamidine Is a Potent Inhibitor of [$^3$H] Idazoxan Binding to Imidazoline I$_2$Receptors", (1999) Ann. NY Acad. Sci. 881:110–113.

Woodle "Poly(ethylene glycol)–Grafted Liposome Therapeutics" in American Chemical Society Sym. Series 680 (1997) Ch. 5 pp. 60–81.

Yeh et al. "Pharmacokinetic Interaction Between Intravenous 2',3'–Dideoxyinosine and Pentamidine in Rats", (1996) Pharm. Res. 13(4):628–632.

Zalipsky "Chemistry of polyethylene glycol conjugates with biologically active molecules", (1995) Advanced Drug Delivery Reviews 16:157–182.

Zalipsky et al. "Introduction to Chemistry and Biological Applications of Poly(ethylene glycol)", in) American Chemical Society, Sym. Series 680 (1997) Ch. 1 1–13.

Zhao et al. "Novel Degradable Poly(ethylene glycol) Esters for Drug Delivery"in American Chemical Society, Sym. Series 680 (1997) Ch. 28 458–472.

Zhao et al. "Small Changes in Cationic Substituents of Diphenylfuran Derivatives have Major . . . Duplexes", (1995) J. Bioorg. Med. Chem. 3(6):785–794.

AMPHIPHILIC POLYMERIC MATERIALS

CROSS-REFERENCE TO RELATED APPLICATION

This invention claims the benefit of U.S. Provisional Application No. 60/232,937, filed Sep. 15, 2000, incorporated by reference in its entirety.

STATEMENT AS TO FEDERALLY SPONSORED RESEARCH

This invention was made with Government support under National Institutes of Health Grant No. 9-R44-GM52363-02. The Government has certain rights in the invention.

FIELD OF THE INVENTION

This invention relates to new drug delivery vehicles, and more particularly to novel micellar amphiphilic polymers that include PEG esters.

BACKGROUND OF THE INVENTION

A large number of drugs are utilized in cancer treatment and other pharmaceutical applications. Drug delivery vehicles are needed to efficiently deliver these drugs to a variety of sites in the body, dependent on the specific disease to be treated. Given that many drugs used to treat cancer, bacterial and viral infections, and diseases such as AIDS are highly toxic and/or have other unfavorable properties such as low solubility in blood or other aqueous solutions, rapid metabolism, or uneven biodistribution, strategies aimed at reaching therapeutic levels of drugs into infected cells are needed. An ideal drug delivery system would: (i) be adaptable to a variety of therapeutic drugs to produce drug-specific vehicles, (ii) have low to zero immunogenicity, (iii) have low clearance by organismal defense mechanisms, (iv) have high stability, even when complexed with a drug, in a physiological milieu, (v) have good shelf life and stability in room temperature storage, (vi) yield only nontoxic byproducts upon metabolism, (vii) be delivered into non-lysosomal compartments, to minimize degradation of the drug, and (viii) have the potential to be targeted to a specific site.

Due to their natural uptake by various cells, the potential of liposomes to be used as drug delivery vehicles has been long recognized (see, e.g., Désormeaux et al., *J. Drug Targeting*, 6(1):1–15, 1998). However, the use of liposomes has also been limited by their immunogenicity, antigenicity, thrombogenicity, cell adherence, and protein absorption characteristics. Although a number of strategies have been devised to improve targeting of drugs to tumor and disease sites, a need still exists for better alternatives.

SUMMARY OF THE INVENTION

The invention is based in part on the discovery of polymers that can complex with certain types of therapeutic drugs and transport those drugs across cell membranes in cell cultures with demonstrable therapeutic activity. The polymers are designed to overcome some of the known problems of liposomes as drug carriers. The polymers can be used in the development of physiologically stable, non-leaking, non-immunogenic, efficacious and safe targetable drug delivery systems (e.g., for delivery of anti-HIV or anticancer drugs).

In general, the invention features a polymer having the structure:

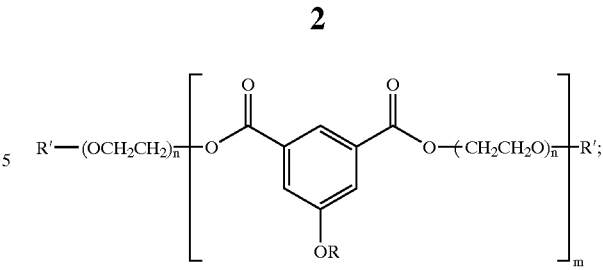

where R is hydrogen, a linear or branched alkyl group (e.g., methyl, ethyl, propyl, isopropyl, butyl, pentyl, hexyl, or isomeric alkyl group, C8–C16 alkyls, or higher alkyl, or aralkyls such as benzyl), a linear or branched alkenyl group (e.g., ethenyl, propenyl, or higher alkenyls), or an aryl group (e.g., phenyl), where the alkyl, alkenyl, or aryl group can be either unsubstituted or substituted with one or more heteroatomic functional groups (e.g., a carboxylate group, a carboxylic acid group, an amino group, an ammonium group, an alkoxyl group, or a hydroxyl group, or other nitrogen, oxygen, or sulfur-containing groups); R' is hydrogen, folic acid, phosphatidylethanolamine, a glycolipid, an indole-containing compound, or other acyl group, antibody fragment, chemomimetic functional group, immunoconjugate, or ligand for a biological target, or

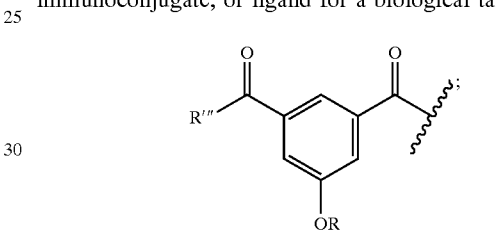

where R''' is a hydroxyl group, an alkoxyl group (e.g., OCH3, O-epitope), or a primary or secondary amino group (e.g., glucosamine, mannosamine, galactosamine); n is at least 1 (e.g., 1, 2, 3, 4, 5, 9, 13, 20, 34, 50, 100, 200, 500 or more); and m is at least 1 (e.g., 1, 2, 3, 4, 5, 10, 20, 50, 100, 200, 500 or more).

The invention also features a method for making the polymer. The method includes the step of reacting a dialkyl-5-hydroxy-isophthalate or a dialkyl-5-alkoxy-isophthalate with a polyethylene glycol.

Another embodiment of the invention features a polymer having the structure:

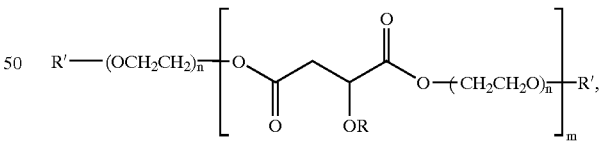

where R and R' are defined as above.

The invention also features a method for making this polymer. The method includes the step of reacting a dialkyl-2-hydroxymalate or a dialkyl-2-alkoxymalate with a polyethylene glycol.

The polymer can be a polymer of either of the above structures that forms micelles in aqueous or organic solutions. A solution that includes a solvent and such a polymer, wherein the polymer is present at a concentration at or above its critical micelle concentration, is also contemplated to be an aspect of the invention.

Another aspect of the invention is a method of enhancing the solubility of a compound, or of increasing the effectiveness or potency of a drug. The method includes the step of complexing the compound or drug with either of the above polymers to render the compound more soluble, effective, or potent. Where the polymer has a receptor ligand (e.g., an antibody or antigen fragment such as Fab or Fab2'; or RGD or an RGD-mimic) recognized by a particular cell type, covalently attached to it (e.g., at position R'), the invention also features a method of targeting a drug to a particular cell type.

The invention also features a composition that includes a complex of either of the above polymers and a drug. The composition can also include an aqueous or organic solution, in which the polymer/drug combination is soluble. The drug can be, for example, a steroid, an anticancer drug, an antibiotic drug, or an antiviral drug. Thus, for example, the drug can be camptothecin, etoposide, zidovudine (AZT), didanosine (ddl), nevirapine, delavirdine, nelfinavir, saquinavir, neomycin, kazugamycin, thorstrepton, erythromycin, taxol, betulinic acid, doxorubicin, or carmustine.

The invention also features a method of administering a drug to a patient (e.g., a patient having a disease such as cancer, cystic fibrosis, an HIV infection, or other bacterial or viral infection. The method includes the step of administering to the patient an effective amount of the composition, together with a suitable excipient.

Yet another aspect of the invention features a gene delivery vehicle that includes a gene or nucleic acid complexed with either of the above polymers. Optionally, an adjuvant can be added to the vehicle.

The invention provides several advantages. For example, the polyethylene glycol (PEG) grafted surfaces of the new polymers improve their long-term stability in plasma, and reduce their immunogenicity, antigenicity, thrombogenicity, cell adherence, and protein absorptivity. The new polymers have many of the advantages associated with liposomes, but share few of their disadvantages. Like liposomes, the new polymers have a spherical micellar structure that mimics the structure of cell membranes. The new polymers can also carry water- or lipid-soluble drugs at a higher drug-loading capacity than is generally possible by conjugation of the drug to a single polymer chain.

The new polymers can form conjugates with natural small molecules to target specific sites. The polymers' molecular structure can be systematically varied to produce a range of well-defined polymeric structures, for example, to result in a range of hydrophilic, hydrophobic, and complexing properties. Thus, numerous closely related structures can be prepared, each having properties optimized for individual drugs rather than having a general structure that would be useful for some drugs but not for others. The new drug delivery systems are, therefore, adaptable to particular drugs, avoiding the need for drugs to be adapted to a particular liposome preparation.

Preparations including the new polymers can provide high therapeutic efficacy at relatively low dosages, thereby reducing toxicity. The new polymers are particularly beneficial for delivery of highly toxic drugs such as anti-HIV drugs. Complexes of the new polymers with antiviral drugs, for example, can decrease the drugs' IC50 (i.e., the drug concentration required to produce 50% inhibition of virus production by a cell line) by 10- to 150-fold or more. Additionally, the long-lived micellar formulations can permit maintenance of therapeutic concentrations with less frequent dosing.

The new polymers also allow delivery of the multiple drug components of a multi-drug therapeutic system (e.g., highly active anti-retroviral therapy, "HAART") in a single delivery vehicle. Alternatively, the combinations of the new polymers can be used, each optimal for one or more components of a multi-drug regimen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The new polymers include amphiphilic esters of PEG and either substituted isophthalic acid derivatives or substituted malic acid derivatives. These polymers form micellar structures with a PEG surface, and are able to encapsulate drugs such as camptothecin, etoposide, and other anticancer, antibiotic, antiviral, and related drug molecules in aqueous media. Conjugate moieties can be attached to the polymers, for example, to improve selectivity of drug delivery or of drug encapsulation.

The individual polymer molecules are able to fold in aqueous media into a structure much like a surfactant micelle or a folded protein, in which the hydrophobic moieties are buried in the structural core and hydrophilic moieties a found on the surface. In addition, multiple polymer molecules can aggregate to form larger micellar structures (i.e., when the polymer concentration is in excess of the polymer's critical micelle concentration (CMC)). The cooperative interactions with other polymer molecules in such a micelle can enhance stability of the micelle over that attainable with micelles or liposomes made from simple low molecular weight compounds.

The polyethylene glycols and their derivatives that are used as hydrophilic polymer backbones are essentially non-immunogenic, and are capable of reducing immunogenicity of complexed drugs. They are also easily copolymerized with diacids such as isophthalic acid and malic acid, without cyclization side reactions.

The metabolic byproducts of malic acid, polyethylene glycol, and possibly isophthalic acid and derivatives, are all expected to be non-toxic. Those new polymers that include malic acid are also labile to low pH. Thus, if the polymer-drug complex is taken into a microsome or endosome, the polymer can be hydrolyzed, leading to swelling and rupture of the microsome or endosome due to uptake of water by the newly created carboxylic acid groups. The malic acid-containing polymers can thereby deliver the drug into the cytoplasm.

The polymers have terminal hydroxyl or carboxyl groups that can provide attachment points for epitopes, antibody fragments, chemomimetic functional groups, immunoconjugates, and/or ligands for biological targets. Thus, for example, folic acid residues, phosphatidylethanolamine, glycolipids (e.g., monosialoganglioside or phosphotidylinositol), glucosamine, mannosamine, indole-containing acids, galactosamine, or other target moieties (such as bioactive peptides, monoclonal antibodies or their fragments, small ligands known to bind to specific receptors on cells or in tissues or organs) can be attached, to target the complexed drugs to a specific tissue, cell type, or organelle, or to improve their circulation times in plasma.

The hydroxyisophthalate or hydroxymalate starting reagents can allow attachment of many types of pendant groups to their hydroxyl group, including alkyl or alkenyl chains, aryl groups, carboxyl-containing groups, amino groups, ammonium groups, and additional hydroxyl groups. By appropriate choice of the pendant group functionalities, it is possible to improve the polymers' interaction with complexed drugs. For example, a carboxyl-containing functional pendant group can interact with nitrogen bases (e.g., primary, secondary, or heterocyclic amines), and can form Schiff bases under appropriate conditions. By choosing appropriate encapsulation conditions, the resulting structure can be formed in such a way that the drug is well held in the core of the micelle, protected from the physiological milieu. As another example, a carboxylic acid group on the drug can be ion-paired with a pendant amine (e.g., a secondary or tertiary amine). The resulting ion pair can be formed in such a fashion that it resides substantially within the core of the micelle. Such pendant groups can be incorporated into the polymer with relative ease, using well-known synthesis methods. Thus, the polymers can be readily tailored to create vehicles that meet the specific requirements of a given guest drug molecule.

Preparation of the New Polymers

The new polymers are prepared by transesterification condensation polymerization of alkoxyisophthalate esters 14 using polyethylene glycols (PEGs) 16 according to Equation 1:

EQUATION 1

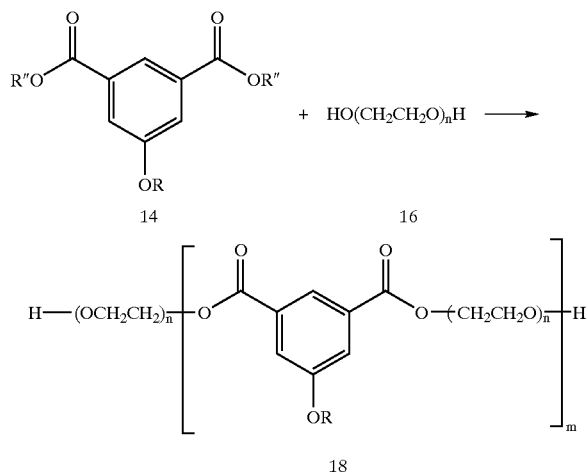

The reactions can be carried out at temperatures ranging from about 100° C. to about 300° C. (e.g., 110–200° C.) for about 5 minutes to about 50 hours (e.g., 4–6 hours). Metal compounds (e.g., dibutyltin diacetate) that have carboxy, alkoxy, or other exchangeable groups can be used as catalysts. Optionally, a solvent (e.g., a high boiling (e.g., >200° C.) solvent) can be used. The alkoxyisophthalate esters 14 themselves can be prepared by alkylation of hydroxy isophthalate esters 10 with alkylating agents 12 according to Equation 2. The reaction can be carried out under mildly basic conditions (e.g., using sodium or potassium carbonate to remove the phenolic hydrogen). The alkylating agent generally includes a good leaving group X, such as a halide (e.g., Cl, Br, or I). The reaction can be carried out at between about room temperature (e.g., 25° C.) and about 200° C. (e.g., 70–80° C.) for about 1 to 24 (e.g., 5–6 hours). A polar solvent (e.g., dimethylformamide, "DMF", or dimethyl sulfoxide, "DMSO") can be used.

EQUATION 2

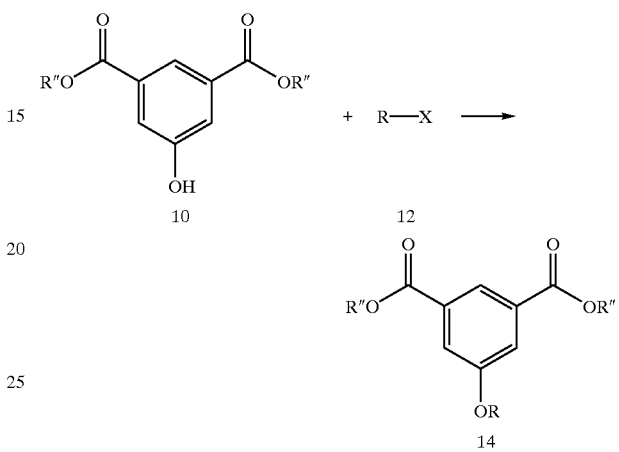

In Equation 2, R can be hydrogen, a linear or branched alkyl group, a linear or branched alkenyl group, or an aryl group, where the alkyl, alkenyl, or aryl group can be unsubstituted or substituted with one or more heteroatomic functional groups such as alcohols, amines, carboxylic acids and their derivatives. R' can be hydrogen, an antibody fragment, a chemomimetic functional group, an immunoconjugate, or a ligand for a biological target. n is generally 1 to 200 or more (e.g., 1, 2, 3, 4, 9, 13, 10, 20, 34, 50, 100, 200, 500 or more, or intermediate ranges); and m is generally 1 to 100 or more (e.g., 1, 2, 3, 4, 5, 10, 20, 50, 100, 200, 500 or more, or intermediate ranges). In general, a higher value for n yields a more hydrophilic polymer; the ability to vary n thus affords control over the hydrophilic/hydrophobic balance of the polymers.

Polyethylene glycols and alkoxyisophthalate esters of various molecular weights can be used, depending on the properties desired of the liposomes. Thus, for example, the hydrophobic character of the polymers can be controlled through selection of an alkoxy group having the desired hydrophobicity. In general, larger pendant alkyl groups (e.g., octyl, decyl, dodecyl, tetradecyl, hexadecyl, octadecyl, dodecyl, and higher alkyls) yield more hydrophobic polymers. The hydrophilicity of the polymers is directly proportional to the molecular weight of the PEG starting material.

The polymers can be characterized, for example, using various analytical methods, including Fourier transform infrared (FFIR) spectroscopy and nuclear magnetic resonance (NMR) spectroscopy. The solution behavior and molecular weight of the polymers can be determined by viscometry or gel permeation chromatography. The critical micelle concentrations (CMC) of the polymers can be determined by surface tension techniques. For example, surface tension can be measured using a surface tensiometer (e.g., a Fisher Scientific Surface Tensiomat 21). A plot of surface tension (in dynes/cm) vs. concentration can be prepared; a change in slope in the plot indicates CMC. The sizes and shapes of the polymeric micelles can be analyzed using scanning electron microscopy (SEM) or dynamic light scattering techniques.

The polymers can be end-capped with folic acid or other epitopes, small ligands, chemomimetic analogs (e.g., indole-containing compounds), antibody fragments, antibodies, arginine-glycine-aspartic acid (RGD) analogs for targeting integrins, or other targeting moieties by reaction of the polymers with the folic acid or other end-capping moiety. Several mild reaction chemistries for condensing terminal hydroxyl groups in the polymers with carboxylic acid groups in such end capping groups are well known. Examples include the use of water scavengers such as carbodiimides such as dicyclohexylcarbodiimide (DCC), 1-ethyl-3-(3-dimethylaminopropyl-carbodiimide (EDAC), or carbonyldiimidazole, with or without additional participation of activators such as N-hydroxysuccinimide. Other methods that can be used include conversion of the carboxylic acid group to an acid anhydride or acyl halide, followed by reaction with the hydroxyl group. The same reactions can be also be applied where the carboxylic acid group is the polymer's terminal group and a hydroxyl group or secondary amino group is present on the end-capping moiety.

In a typical procedure for alkylating the hydroxyisophthalates 10 (e.g., R=CH$_3$, H, or Na), an alkyl halide 12 (e.g., an alkyl bromide or chloride such as octyl bromide) is added under basic conditions to form the corresponding alkoxyisophthalate 14 (e.g., R'=butyl, octyl, decyl, dodecyl, tetradecyl). The alkoxyisophthalates 14 are then reacted with PEGs 16 (e.g., n=4, 6, 9, 13, 20, 34) to form polymers 18.

As an alternative method, isophthalates can be pegylated enzymatically (e.g., using a lipase enzyme). This method can be used with both unfunctionalized (e.g., R=hydrogen or alkyl, alkenyl, aryl) and functionalized isophthalates (e.g., R=alkoxyalkyl or other functionalized moieties).

In certain of the examples described below, the polymers were prepared by a two-stage heating sequence using dibutyl tin diacetate as a catalyst. The polymer structures were characterized by carbon and proton NMR and FTIR spectroscopy. The viscometric properties of the polymers in aqueous solution were analyzed in the dilute (<0.1 w/v %) and semi-concentrated (5.0 w/v %) ranges. The intrinsic viscosity was determined, and the polymers were found to have molecular weights in the range of 4,500 to 32,000 g/mole, which can be converted to the degree of polymerization (DP), since the molecular weight of each repeat unit is known for each polymer. Polymers formed with dimethyl isophthalate (DMI) had higher average DP (i.e., 20 to 27) than did those formed with dimethyl butyloxyisophthalate (DMBI; DP=10 to 15) or dimethyl octyloxyisophthalate (DMOI; DP=8 to 11). The dilute solution properties were found to be dominated by the PEG portion of the polymer. The semi-concentrated range (as determined in a Wells-Brookfield cone and plate viscosometer) exhibited pseudoplastic behavior, with viscosity decreasing with increasing shear rate.

The polymers self-associate into micelles at concentrations above their respective critical micelle concentrations (CMCs). The CMCs of the polymers were determined by plotting surface tension (i.e., using a Fisher Scientific Surface Tensiomat 21) against concentration, and identifying the break point. The values obtained ranged from 0.25 to 2.5 mM, with the lower values corresponding to the higher molecular weight polymers.

The micelles were spherical in shape, based on scanning electron microscopy (SEM) results. Static light scattering (SLS) studies on the polymers showed radius of gyration of micelle particle in the range of 30 to 50 nm (diameter=60 to 100 nm), and association numbers of 80 to 100 when the light scattering molecular weights were divided by the number average molecular weights, as determined by viscosity and gel permeation chromatography. These results were consistent with data obtained using dynamic light scattering techniques, which indicated micellar diameters of 58 to 100 nm.

Folic acid was coupled to the ends of the polymer chains using dicyclohexylcarbodiimide coupling, resulting in approximately 90% of the polymers being capped with the folic acid when analyzed by ultraviolet (UV) spectroscopy. Similarly, acetylsalicylic acid was coupled with the polymers, using an acyl halide reaction.

Malate-containing polymers can be prepared by the same procedure as described above for the isophthalate-containing polymers (i.e., by substituting hydroxymalates for the hydroxyisophthalates 10).

Complexation of the New Polymers with Drugs or Other Small Molecules

Complexation of the polymers with benzo[a]pyrene, camptothecin, etoposide, and other small molecules can be accomplished by dissolving the polymers and small molecules in an appropriate organic solution (e.g., chloroform) followed by slow evaporation of the solvent (e.g., by coating a thin film of the solution on a glass surface, then drying under vacuum). The residue can then be taken up in endotoxin-free water and the uncomplexed small molecules removed by centrifugation (for water insoluble small molecules) or dialysis (for water soluble molecules). The final small molecule-polymer complex product can be purified, for example, by high-pressure liquid chromatography (HPLC).

Polymer-small molecule complexes were also formed by mixing the polymers and the small molecules in the solid state, melting the polymers, and then subsequently cooling the mixtures.

Anti-HIV drugs such as zidovudine (AZT), didanosine (ddI), nevirapine, delavirdine, nelfinavir, and saquinavir can similarly be complexed with the new polymers. Other anti-cancer drugs such as taxol or betulinic acid can similarly be complexed.

Screening of the Polymer-Small Molecule Complexes for Biological Activity

A human cell line such as OM10.1 (Butera et al., *AIDS Res. Hum. Retroviruses*, 8:991–995, 1992), which is chronically infected with HIV-1, can be used to test the antiviral activities of the new polymer encapsulated drugs (e.g., using the method of Critchfield et al., *AIDS Res. Hum. Retroviruses*, 12:39–46, 1996). Upregulation of HIV-1 expression can be stimulated in OM10.1 with the presence of a cytokine such as TNF-alpha. The drug can be added to the OM10.1 cell cultures simultaneously with the cytokine. Each day (e.g., for four days), culture supernatants can then be tested for HIV-1 p24 antigen levels, for example, using a commercially available ELISA kit (Coulter), and for reverse transcriptase (RT) activity, using a commercially available chemiluminescent ELISA RT assay such as that sold by Boehringer Mannheim, each according to the manufacturer's instructions. For initial screening of the dose-response profile against HIV-1 expression by the cytokine-stimulated OM10.1 cells, each drug can be tested at 10–15 concentration points bracketing the known IC$_{50}$ for each free drug over a 4 magnitude range. Duplicate data points can be collected at each concentration. For each drug examined three different dose-response profiles can be performed, including: the free drug, the polymer encapsulated drug, and the polymer alone.

An efficient model system to monitor the spread of HIV-1 from infected cells to uninfected ones in culture has been described previously (Rabin et al, 1996; Sato et al., 1992). Co-cultivation on uninfected and HIV-infected T lymphocytes results in rapid cell fusion and transmission of viral infection. HIV infected MT-4 or CEM cells ($1 \times 10^6$ donor cells) are co-cultured with uninfected recipient cells ($4 \times 10^6$ cells), and monitored at 24-hour intervals over a two to four week period. A fixed number of uninfected cells can be added biweekly. The initial ratio of HIV infected to uninfected cells can be adjusted to ensure that the experiments are performed within the detection limits of the virus production assays. Virus production can then be monitored by following the p24 antigen in the cell supernatant using a standard ELISA assay (Coulter). Virus replication can be monitored by following the time profile of RT activity using a standard ELISA assay. Cellular toxicity can be monitored spectrophotometrically using the tetrazolium dye XTT. The free drug's and polymer-complexed drug's $EC_{50}$, $IC_{50}$, therapeutic index, and selectivity index can be determined as described (Halliday, et al, *Antiviral Res.*, 33;41–53, 1996), to evaluate the effect of encapsulation on drug activity.

The multiplicity of infection (MOI) can be varied in 0.01 to $128 \times/10^5$ cells (Halliday, et al., *Antiviral Res.*, 33;41–53, 1996), as determined by endpoint titration, to determine its effect on the activity indices.

As a complementary approach, the antiviral activity of complexed drug can be tested and compared with the free drug, for example, in a cell system that monitors a spreading HIV infection in isolated human PBMCs (Rabin et al., *Antimicrob. Agents Chemotherap.*, 40:755–762, 1996). Uninfected human PBMC can be cultured in non-toxic doses of either encapsulated drug or free drug, stimulated with phytohemagglutinin (PHA), infected with a specific HIV viral stock at a specific MOI, and passaged biweekly, in the presence of the same drug (or encapsulated drug) as used for culturing for several weeks. At regular intervals, fresh uninfected human PBMCs can be added to replenish the cultures. The drug under test can be added as replenishment bi-weekly. Virion production can be monitored post-infection at regular intervals (e.g., every 3 days) using a rapid virion-associated reverse transcriptase assay (Goff et al., *J. Virol*, 38:239–248, 1981). The viral structural protein p24 can then be quantified using a standard ELISA assay (Coulter). If warranted, quantitative PCR can be used to monitor the level of HIV-1 DNA during the course of infection when the level becomes undetectable by the p24 and RT assays.

The effect of the polymer alone and the encapsulated drug on cell growth and on PHA stimulation can be assessed prior to these activity evaluation experiments using established techniques (Chow, et al., *Nature*, 361:650–654, 1993). The MOI can be varied in 0.01 to $128 \times/10^5$ cells (Halliday et al, *Antiviral Res.*, 33;41–53, 1996), as determined by endpoint titration, to determine its effect on the activity indices.

The antiviral activity of mixtures of pre-encapsulated drug regimens can also be assayed against mixtures of free drug regimens (e.g., HAART or other clinical regimens) particularly with reference to production of mutant virions.

Methods of Treatment

Complexes of the new polymers with drugs can be administered, for example, in a pharmaceutically acceptable carrier such as physiological saline, in combination with other drugs, and/or together with appropriate excipients. The complexes can, for example, be administered by injection, intravenously, intraarterially, subdermally, intraperitoneally, intramuscularly, or subcutaneously; or orally, buccally, nasally, transmucosally, in an ophthalmic preparation, or by inhalation, with a dosage ranging from about 0.001 to about 10 mg/kg of body weight every 8 to 120 hours, or according to the requirements of the particular drug. However, as is well known in the medical arts, dosages for any one patient depends upon many factors, including the patient's weight, body surface area, age, the particular compound to be administered, sex, time and route of administration, general health, and other drugs being administered concurrently. Also, because the polymers can hold both hydrophilic and hydrophobic drugs in their interiors until they are delivered into cells, and can aid the drugs in evading the metabolic (e.g., clearance) and immune systems, the dosages required may be less than the dosages required of traditional formulations. The effectiveness and/or bioavailability can be increased 1000-fold or more in some cases by the new polymers.

The complexes can additionally be administered prophylactically for prevention of disease.

For targeted, specific, or directed drug delivery, receptor ligands can be covalently attached to the ends of the polymers to direct the polymers specifically to a particular cell type. Thus, for example, monoclonal antibodies or their fragment epitopes (e.g., Fab2' or Fab) can be covalently linked to the polymers. Enhanced specificity can also be attained by using ligands that bind to receptors that are overexpressed in certain cell types. General cell attachment can be enhanced by attaching ligands that mimic the ability of the cell-attachment peptide sequence RGD (arginine-glycine-aspartic acid) or the peptide RGD itself at the polymer termini.

The new polymers can also be used in the delivery of nucleic acids (e.g., RNA or DNA; gene therapy) or peptides (e.g., oligopeptides, proteins, or enzymes). Such delivery can be targeted or non-targeted. The polymers can complex with the nucleic acid molecules, for example, to enhance transient gene expression, relative to traditional gene therapy approaches (e.g., cationic liposomes).

The pendant groups are optionally modified to create specific covalently or non-covalently reactive cores in the polymer micelle. Such modifications can be used to enhance the polymers' ability to hold and carry into cells cationic or amine-containing drugs, or to carry and deliver into cells anionic drugs or anionic polymers such as DNA and RNA.

The amphiphilic polymers' ability to act as surfactants enables them to be used as adjuvants for nasal sprays and for pulmonary delivery of drug agents or DNases for treatment of cystic fibrosis. The polymers can also be absorbed by mucosal routes (e.g., sublingual or duodenal absorption), as well by across abraded skin.

In pulmonary drug delivery methods, the polymers can play a dual role, being able to both carry drugs into the polymer micelles and form small enough micellar sprays (mists) to reach into the deep lung tissue.

The new polymers can also be used in ophthalmic preparations. Because they are polymeric, they do not evaporate quickly, as do certain other viscous solutions used for this purpose. In addition, the PEO backbone can absorb moisture from air, thereby keeping the eye well watered. The polymers can be used to make micellar preparations of ophthalmological drugs and can function as adjuvants.

Thus, the polymers can protect drugs (including nucleic acids and peptides) from physiological fluids, as well as protecting physiological systems from the drug molecules. The polymers can carry drugs across cell membranes and deliver them into cells to create a high effective concentration of drug. The polymers can be used to target specific cell types (e.g., ligand-modified polymers) for the purpose of attacking specific cell types. For example, the polymers can be used in the delivery of anticancer drugs to kill cancer cells, in the delivery of growth factors (e.g. erythropoeitin, G-CSF, GM-CSF) to appropriate cells such as the progenitor cells in the bone marrow or the spleen, or in the delivery of effectors to affectable cells.

The complexes can also be used in non-therapeutic medical applications, such as in diagnostic procedures, or as catalysts for either biological or synthetic chemical reactions.

Other Biological and Biochemical Applications of the New Polymers

The new polymers can be used in other biological and biochemical applications. For example, the new polymers can be used for solubilization of membrane proteins into aqueous solutions, with minimal loss of activity. The polymers can also be used in the crystallization of membrane proteins.

Non-Biological Applications of the New Polymers

Because the polymers are, in general, excellent surfactants, they can be used in numerous other applications. For example, they can be used in the manufacture of aqueous dye or pigment systems, including aqueous or organic insoluble dyes and pigments. They can be used in the clean-up of organic fluid spills, including removal of oils and/or carcinogens. Aqueous solutions containing the polymers can be used in the cleaning of machine parts and other articles (e.g., semiconductor wafers, flexible (e.g., plastic) or rigid (e.g., copper-based) printed circuit boards, crude oil pipelines) to remove insoluble materials.

EXAMPLES

The invention is further described in the following examples, which do not limit the scope of the invention described in the claims.

Example 1

Preparation of Dimethyl-5-Octyloxyisophthalate (DMOI) and Dimethyl-5-Butyloxyisophthalate (DMBI) Esters Dimethyl-5-hydroxyisophthalate (5.0 g, 23.8 mmole; Aldrich Chemical Co., Inc., Milwaukee, Wis.) and potassium carbonate (6.5 g, 47.2 mmole) were added to 200 ml dimethylformamide (DMF) and stirred for 1 hour at 80° C. under a nitrogen atmosphere. To this mixture was added a solution of 1-bromooctane (4.6 g, 23.8 mmole) in 50 ml DMF, and the resulting solution was stirred for six hours. The DMF was then removed under reduced pressure, and water was added to the residue. The mixture was then extracted with dichloromethane (DCM; 5×30 ml), and the DCM extracts were dried with magnesium sulfate and evaporated to yield dimethyl-5-octyloxyisophthalate ester as a white powder, which was then recrystallized from methanol. The identity of the compound was confirmed by carbon and proton NMR, as well as by FTIR spectroscopy.

Dimethyl-5-butyloxyisophthalate was prepared according to the same procedure, substituting 1-bromobutane for 1-bromooctane.

Example 2

Preparation of Isophthalate-PEG Polymers

A mixture of the dimethyl-5-octyloxyisophthalate ester prepared in Example 1 (15 mmole), PEG-1500 (n=34; 30 mmole), and dibutyltin diacetate (5% w/w) was stirred at 120–130° C. under a nitrogen atmosphere for 2 hours. The mixture was then heated to 200° C. for 30 minutes. The reaction was allowed to continue for an additional 2 hours at 200° C. under reduced pressure (<1 mmHg). The crude product was dissolved in tetrahydrofuran (THF), then precipitated with hexane. The product was dissolved in water and dialyzed (MW cutoff=1 kDa) to remove unreacted monomer units. Polymer yields were greater than 80%. The final product was characterized as dimethyl-end-capped 5-octyloxyisophthalate-PEG-1500 (PEG-500-DMOI) with greater than 99% purity by carbon and proton NMR, as well as by FTIR spectroscopy.

Other polymers were prepared by the same procedure, using dimethyl-5-hydroxyisophthalate and dimethyl-5-butyloxyphthalate esters in place of the octyloxy compound, and/or tetraethylene glycol, hexaethylene glycol (HEG), PEG-400 (n=9), PEG-600 (n=13), or PEG-900 (n=20) in place of the PEG-1500. Except for HEG, the value of n for the PEGs is an average value supplied by the vendor. Because of the polydispersity in the starting PEGs, the degree of polymerization (DP) of the final polymers is likely to show greater polydispersity than would be expected if a discrete PEG were used. The polydispersity of the starting PEGs can be minimized, if desired, for example, by gel permeation chromatography (GPC) fractionation.

By altering the molar ratio of the alkoxy dimethyl isophthalate and the PEG species, polymers were obtained with either exclusively hydroxyl-terminated chains or exclusively carboxyl-terminated chains.

Example 3

Preparation of Folic Acid End-Capped PEG-500-DMOI Polymer

A solution of DCC (0.165 g, 0.8 mmole) in dry dimethylsulphoxide (DMSO) was added dropwise to a solution of folic acid (0.3820 g, 0.8 mmole) in dry DMSO. The reaction was stirred at room temperature. A solution of a hydroxyl-terminal PEG-1500-DMOI prepared according to the procedure of Example 2 (6.80 g, 0.4 mmole) in dry DMSO was added dropwise to the DCC/folic acid mixture, and the resulting solution was stirred overnight. The DMSO was evaporated under reduced pressure, and the residue was dissolved in a 0.03 M aqueous solution of sodium hydroxide. The aqueous solution was then extracted with chloroform and cyclohexane, neutralized with aqueous hydrochloric acid, and dialyzed for one hour. The water was removed under reduced pressure and the product was dried in vacuo overnight. The resulting greenish-yellow powder was analyzed by carbon and proton NMR and FTIR spectroscopy, and confirmed to be the desired end-capped derivative.

Example 4

Complexation of Benzo[a]Pyrene, Camptothecin, or Etoposide with PEG-1500-DMOI Benzo[a]Pyrene (BP), a dye and potent carcinogen, was chosen as a hydrophobic model because BP encapsulation within aqueous micelles of the PEG-1500-DMOI polymer can be monitored by UV absorption spectroscopy. The amount of dye encapsulated in the micelles was readily determined by UV spectroscopy since an absorbance signal due to benzo[a]pyrene appeared in the 340–450 nm region only when the dye was solubilized within the aqueous micelle. Different concentrations of dye were prepared in dichloromethane and each was added to a constant amount of polymeric micelle solution (1 ml of 100 mg/ml). Polymer-dye complex films were cast on glass and dried under vacuum at room temperature overnight. The films were then removed and redissolved in water by sonication at 35° C. for 10 minutes, and purified by filtration from excess dye. A homogenous, stable solution of the dye was formed at concentrations of more than 0.25 wt %, indicating partitioning of the dye into the micellar core. The maximum loading capacity of the dye was 0.88% (w/w). Benzo[a]pyrene complexes with PEG-1500 polymers were found to be stable for more than a month at room temperature. A partition coefficient of $5 \times 10^4$ was determined, indicating strong partitioning. Experiments with polymers formed with dimethyl-hydroxyisophthalate (DMI) or DMI linkers did not allow significant encapsulation of BP within their micelles.

In other experiments using this encapsulation method, PEG-1500-DMOI was complexed with either camptothecin or etoposide by combining the polymer and drug in a 4:1 chloroform/methanol mixture, then evaporating the resulting mixture overnight at room temperature under vacuum. The residue was treated with 5 ml water and filtered to remove any uncomplexed camptothecin. The solution was then examined with UV spectroscopy to determine the amount of complexed drug. The loading was found to be 1.25% and 3.1% (w/w), respectively.

A second method to form drug-polymer complexes was also developed. In this method, equimolar aqueous solutions of the polymer and the drug were mixed at room temperature and then diluted further with water. Complexes of PEG-1500-DMOI with camptothecin were formed by each of these methods and studied by 2D-NMR. When the polymer-drug complex was formed in chloroform, the drug interacted exclusively with the pendant alkyl chains of the polymer. When the polymer-drug complex was formed by mixing in water, the drug interacted with the alkyl chains as well as the ethylene glycol moieties of the backbone.

Example 5

Complexation of Neomycin, Kazugamycin, Thiostreipton, or Erthromycin with PEG-1500-DMOI, and Biological Assays Neomycin, kazugamycin, thiostrepton, and erythromycin were complexed with the polymer at 1:1 molar ratio by mixing equimolar concentrated solutions of polymer and drug, followed by dilution in water. Inhibition of cellular HIV Rev function was examined in several cell lines for both the free drug and the polymer-drug complexes, as follows.

Transfection assays for Rev protein function were performed in COS7 and human macrophage MT4 cell lines as described by Zapp et al. (Cell, 74:969–978, 1993). The HIV-1 Rev protein acts post-transcriptionally to increase the cytoplasmic levels of the gag-pol and env mRNAs. A specific RNA binding site on these mRNA's, referred to as the Rev response element (RRE), is required for Rev function. In this assay system, Rev protein binds to a reporter RNA and transports it from the nucleus to the cytoplasm. The reporter RNA is transcribed from a plasmid containing the HIV env cDNA fused to the reporter gene, the cDNA for the enzyme chloramphenicol acetyltransferase (CAT).

For the Rev function assay, cells were washed twice, 14 hours after transfection, with 1×phosphate-buffer saline (PBS), and then with 1×Dulbecco's modified Eagle's medium (DMEM). Subsequently, 10% fetal calf serum containing the polymer or polymer-encapsulated drug samples was added. The effects of long-term (24 hours) as well as short-term (8 hours) drug treatments on Rev function were examined by CAT activity, beta-galactosidase expression, cell growth and toxicity, and cell morphology. 'Toxicity' was monitored by checking for slowed rates of replication, changes in cell shape and size, and necrosis. Experiments were performed with duplicate samples and independently repeated at least three times.

Yanagida and colleagues reported that 25 $\mu$M of non-encapsulated kazugamycin blocks HIV-1 Rev function in CD4+HeLa cells, with decreased cell proliferation and necrosis occurring at 35 $\mu$M concentration (Zapp, Cell, 74:969–978, 1993). PEG-1500-DMOI-complexed kazugamycin A was found to abolish Rev function at much lower drug-equivalent concentrations (4.2 $\mu$m vs. 25 $\mu$m for free drug), and cell necrosis occurred at 20 $\mu$M, indicating a significant improvement in cell culture drug efficacy, as well as in cell culture therapeutic index due to encapsulation.

In mammalian cell cultures, 1 mM extracellular unencapsulated thiostrepton has no detectable effect on cell growth or cell morphology. However, thiostrepton complexed with PEG-1500-DMOI repressed host cell translation at concentrations as low as 20 $\mu$M (drug-equivalent). At higher concentrations (e.g., 30 $\mu$M), loss of cell viability was seen. Host cell translation was monitored by the expression of inducible β-galactosidase activity; cell viability was monitored spectrophotometrically using XTT dye. Cell death at such low concentrations of encapsulated thiostrepton suggests a significant increase in intracellular drug concentration and disruption of peptide elongation.

Neomycin B complexed with PEG-1500-DMOI was then tested for inhibition of Rev function in chronically infected U1 cells in a cell-cell infectivity assay of HIV replication. The results are shown in Table 1 below.

| Neomycin Treatment | RT-Activity 1E5 cpm/ml | % Viability |
| --- | --- | --- |
| none | 3.20 | 6% |
| Polymer Alone | 1.00 | 19% |
| Encapsulated Drug, 48 h | 0.50 | 34% |
| Encapsulated Drug, 96 h | 0.06 | 45% |

In this study, the number of uninfected cells, total cell viability, and reverse transcriptase (RT) activity were monitored at 24 hour intervals. Uninfected cells ($5 \times 10^4$ or $5 \times 10^5$/ml) were co-cultivated with $HIV_{LA1}$-infected cells ($1 \times 10^5$ or $1 \times 10^6$/ml, respectively-these were infected at MOI=1 following treatment with PHA for 4 hours). After 6 hours, the co-cultures received a single dose of encapsulated neomycin B (15 $\mu$M) or the equivalent amount of polymer alone, as indicated in Table 1. Aliquots (300 $\mu$l) of supernatant were collected at 24 hour intervals, and RT was assayed as described above. Percent viability of uninfected MT-4 cells alone ($1 \times 10^5$/ml) at 7 days post-addition of encapsulated neomycin b was 94.7%. Percent viability of $HIV_{LAI}$-infected MT4 cells in 15 $\mu$M encapsulated neomycin B, 7 days post co-culture, was 83%, with RT activity $<2.3 \times 10^3$ cpm/ml. Viability was monitored spectrophotometrically using the tetrazolium dye XTT. All sample analyses were performed in triplicate.

In this single dose study, PEG-1500-DMOI-complexed neomycin B was found to inhibit HIV production at a concentration that is significantly lower (15 μM) than previously reported for the unencapsulated neomycin B (2,500–5,000 μM), an activity enhancement of at least 150-fold.

In contrast, PEG-1500-DMOI-encapsulated erythromycin showed no significant differences from unencapsulated erythromycin, which is already highly membrane-permeable. Importantly, however, the erythromycin/polymer complex showed no cytotoxicity, suggesting that the cytotoxicity observed for the polymer-drug complexes of neomycin, thiostrepton, and kazugamycin was not caused by the polymer but by the increased intracellular drug concentration.

In general, the polymer delivery vehicles significantly enhanced effectiveness of three drugs, neomycin, kazugamycin and thiostrepton, which act by different mechanisms in the Rev functional assay, over that of the corresponding free drugs.

Example 6

Preparation of Malate-PEG Polymers

Diethyl malate linkers are synthesized with alkyl chains of 8, 10, 12, 14, and 16 carbons, using the methods described for isophthalate linkers in Example 1, and then polymers are made, incorporating malate linkers and the same series of PEGs (n=4, 6, 9, 13, 20 and 34) used in the PEG-isophthalate polymer syntheses in Example 2.

The synthesized polymers are purified as follows. The unreacted acid esters are removed by extraction with organic solvents such as chloroform. The polymer is then further purified by low temperature crystallization from a suitable polar organic solvent such as methanol, ethanol, isopropanol, or THF. The solvent is completely removed by vacuum evaporation in a Buchi Rotavap. Residual unreacted PEG and hydrolyzed acids, if any, are removed by triple dialysis of aqueous solution of the polymer against water using a dialysis membrane with a molecular weight cut-off (MWCO) that guarantees removal of the unreacted PEG. The dialyzed polymer is fractionated for molecular weight if necessary using GPC in an acetonitrile/water gradient or water alone as solvent. The purified fraction is exhaustively evaporated under vacuum to remove the solvent. The dried polymer is weighed to determine yield and is then stored cold (10° C.) and desiccated.

Example 7

Pegylation of Dimethyl-5-[t-butoxy-dodecanyl ether]-isophthalate

Equimolar amounts (i.e., 3 mmol) of dimethyl-5-[t-butoxy-dodecanyl ether]-isophthalate and polyethylene glycol (PEG 1500) in toluene (50 ml) were placed in a round-bottomed flask, and 50 mg of Candida Antartica Lipase (CAL) was added to the mixture. The flask was fitted with Dean-Stark apparatus and a needle was inserted for continuous bubbling of nitrogen (i.e., for methanol evaporation). The reaction mixture was gently stirred at 60° C. The reaction was monitored for the disappearance of the monomer using thin layer chromatography (TLC). After completion of the reaction (about three days), the reaction mixture was filtered to remove the enzyme, and the toluene was evaporated under vacuum. Water was added to the residue with stirring, and the mixture then filtered. The filtrate was subjected to dialysis for three days, and water was again evaporated under vacuum. The residue was freeze-dried, and then analyzed by nuclear magnetic resonance (NMR).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, the new polymers can be used in any application that involves encapsulating compounds to improve their water solubility. Such compounds are not limited to drugs, but also include paints, dyes, cosmetic agents such as melanin, benzoyl peroxide, ultraviolet protection agents (e.g., sunscreens), insect repellants, and botulism toxin (e.g., for use in wrinkle reduction).

What is claimed is:

1. A polymer comprising a structure represented by:

$$\left[ R'\!-\!(OCH_2CH_2)_n\!-\!O\!-\!\underset{\underset{OR}{\big|}}{\overset{O}{\underset{\|}{C}}\!-\!C_6H_3\!-\!\overset{O}{\underset{\|}{C}}}\!-\!O\!-\!(CH_2CH_2O)_n\!-\!R' \right]_m$$

wherein

R is hydrogen, a linear or branched alkyl group, a linear or branched alkenyl group, or an aryl group; wherein said alkyl, alkenyl, or aryl group is unsubstituted or substituted with one or more heteroatomic functional groups;

R' is hydrogen, an acyl group, an antibody fragment, a chemomimetic functional group, an immunoconjugate, a ligand for a biological target, or $$R'''\!-\!\overset{O}{\underset{\|}{C}}\!-\!\underset{\underset{OR}{\big|}}{C_6H_3}\!-\!\overset{O}{\underset{\|}{C}}\!-\!\sim\!;$$

wherein

R''' is a hydroxyl group, an alkoxyl group, or a primary or secondary amino group;

n is at least 1; and m is at least 1.

2. The polymer of claim 1, wherein R is C8-C16 alkyl.

3. The polymer of claim 1, wherein R is substituted with a carboxylate, carboxylic acid, amino or ammonium, alkoxyl, or hydroxyl group.

4. The polymer of claim 1, wherein R' is selected from the group consisting of hydrogen, folic acid, phosphatidylethanolamine, a glycolipid, and an indole-containing compound.

5. The polymer of claim 1, wherein said polymer forms micelles in aqueous or organic solutions.

6. A composition comprising:
a complex of a polymer of claim 1 and a drug.

7. The composition of claim 6, further comprising an aqueous or organic solution, wherein said polymer and drug combination is soluble in said solution.

8. The composition of claim 6, wherein the drug is a steroid, an anticancer, antibiotic, or antiviral drug.

9. The composition of claim 6, wherein the drug is camptothecin, etoposide, zidovudine (AZT), didanosine (ddI), nevirapine, delavirdine, nelfinavir, saquinavir, neomycin, kazugamycin, thorstrepton, erythromycin, taxol, betulinic acid, doxorubicin, or carmustine.

10. A method of making a polymer of claim 1, the method comprising:
reacting a dialkyl-5-hydroxy-isophthalate or a dialkyl-5-alkoxy-isophthalate with a polyethylene glycol to form a polymer of claim 1.

11. A method of administering a drug to a patient, the method comprising:
administering to the patient an effective amount of the composition of claim 6 together with a suitable excipient.

12. The method of claim 11, wherein the patient has cancer.

13. The method of claim 11, wherein the patient has an human immunodeficiency virus infection.

14. A solution comprising a solvent and the polymer of claim 5, wherein the polymer is present at a concentration at or above its critical micelle concentration.

15. A method of enhancing the solubility of a compound, the method comprising: complexing the compound with the polymer of claim 1 to render the compound more soluble.

16. A method of increasing the effectiveness or potency of a drug, the method comprising: complexing the drug with the polymer of claim 1 to form a more effective or more potent drug.

17. The method of targeting a drug to a particular cell type, the method comprising:
complexing the drug with a polymer of claim 1, wherein the ligand for a biological target is a receptor ligand recognized by the particular cell type, thereby targeting the drug to the particular cell type.

18. The method of claim 17, wherein the receptor ligand is an antibody or an antibody fragment epitope.

19. The method of claim 18, wherein the epitope is Fab2' or Fab.

20. The method of claim 17, wherein the receptor ligand is arginine-glycine-aspartic acid (RGD) or an RGD mimic.

21. A gene delivery vehicle comprising:
a gene or nucleic acid complexed with a polymer of claim 1.

22. The gene delivery vehicle of claim 21, further comprising an adjuvant.

23. A polymer comprising a structure represented by:

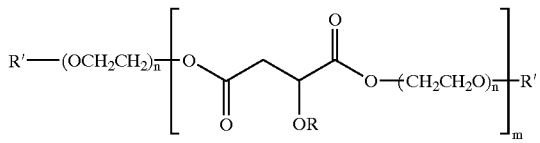

wherein
R is hydrogen, a linear or branched alkyl group, a linear or branched alkenyl group, or an aryl group; wherein said alkyl, alkenyl, or aryl group is unsubstituted or substituted with one or more heteroatomic functional groups;

R' is hydrogen, an acyl group, an antibody fragment, a chemomimetic functional group, an immunoconjugate, a ligand for a biological target, or

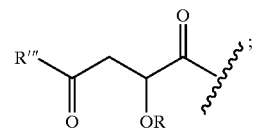

wherein
R''' is a hydroxyl group, an alkoxyl group, or a primary or secondary amino group;
n is at least 1; and
m is at least 1.

24. The polymer of claim 23, wherein R is C8–C16 alkyl.

25. The polymer of claim 23, wherein R is substituted with a carboxylate, carboxylic acid, amino or ammonium, alkoxyl, or hydroxyl group.

26. The polymer of claim 23, wherein R' is selected from the group consisting of hydrogen, folic acid, phosphatidylethanolamine, a glycolipid, and an indole-containing compound.

27. The polymer of claim 23, wherein said polymer forms micelles in aqueous or organic solutions.

28. A composition comprising:
a complex of a polymer of claim 23 and a drug.

29. The composition of claim 28, further comprising an aqueous or organic solution, wherein said polymer and drug combination is soluble in said solution.

30. The composition of claim 28, wherein the drug is a steroid, an anticancer, antibiotic, or antiviral drug.

31. The composition of claim 28, wherein the drug is camptothecin, etoposide, zidovudine (AZT), didanosine (ddI), nevirapine, delavirdine, nelfinavir, saquinavir, neomycin, kazugamycin, thorstrepton, erythromycin, taxol, betulinic acid, doxorubicin, or carmustine.

32. A method of making a polymer of claim 23, the method comprising:
reacting a dialkyl-2-hydroxymalate or a dialkyl-2-alkoxymalate with a polyethylene glycol to form a polymer of claim 23.

33. A method of administering a drug to a patient, the method comprising:
administering to the patient an effective amount of the composition of claim 28 together with a suitable excipient.

34. The method of claim 33, wherein the patient has cancer.

35. The method of claim 33, wherein the patient has a human immunodeficiency virus infection.

36. A solution comprising a solvent and the polymer of claim 27, wherein the polymer is present at a concentration at or above its critical micelle concentration.

37. A method of enhancing the solubility of a compound, the method comprising:
complexing the compound with the polymer of claim 23 to render the compound more soluble.

38. A method of increasing the effectiveness or potency of a drug, the method comprising:
complexing the drug with the polymer of claim 23 to form a more effective or more potent drug.

39. The method of targeting a drug to a particular cell type, the method comprising:
  complexing the drug with a polymer of claim 23, wherein the ligand for a biological target is a receptor ligand recognized by the particular cell type, thereby targeting the drug to the particular cell type.

40. The method of claim 39, wherein the receptor ligand is an antibody or an antibody fragment epitope.

41. The method of claim 40, wherein the epitope is Fab2' or Fab.

42. The method of claim 39, wherein the receptor ligand is arginine-glycine-aspartic acid (RGD) or an RGD mimic.

43. A gene delivery vehicle comprising:
  a gene or nucleic acid complexed with a polymer of claim 1.

44. The gene delivery vehicle of claim 43, further comprising an adjuvant.

* * * * *